(12) United States Patent
Richter et al.

(10) Patent No.: US 9,504,562 B2
(45) Date of Patent: Nov. 29, 2016

(54) SELF-ASSEMBLING MODULAR PERCUTANEOUS VALVE AND METHODS OF FOLDING, ASSEMBLY AND DELIVERY

(75) Inventors: Yoram Richter, Ramat Hasharon (IL); Jacob Richter, Arsuf (IL); Ety Weisz, Kiryat Ono (IL)

(73) Assignee: Valve Medical Ltd., Tel Aviv (IL)

(*) Notice: Subject to any disclaimer, the term of this patent is extended or adjusted under 35 U.S.C. 154(b) by 806 days.

(21) Appl. No.: 12/686,338

(22) Filed: Jan. 12, 2010

(65) Prior Publication Data

US 2011/0172784 A1 Jul. 14, 2011

(51) Int. Cl.
*A61F 2/24* (2006.01)
*A61F 2/844* (2013.01)

(52) U.S. Cl.
CPC .......... *A61F 2/24* (2013.01); *A61F 2/2412* (2013.01); *A61F 2/2418* (2013.01); *A61F 2/2427* (2013.01); *A61F 2/2406* (2013.01); *A61F 2/2409* (2013.01); *A61F 2/844* (2013.01); *A61F 2210/0014* (2013.01); *A61F 2230/0091* (2013.01); *A61F 2250/006* (2013.01)

(58) Field of Classification Search
CPC ...... A61F 2/24; A61F 2/2409; A61F 2/2427; A61F 2/2406
USPC ...................... 623/1.24, 1.26, 2.17
See application file for complete search history.

(56) References Cited

U.S. PATENT DOCUMENTS

| | | | |
|---|---|---|---|
| 5,411,552 A | 5/1995 | Anderson et al. | |
| 5,840,081 A | 11/1998 | Anderson et al. | |
| 6,168,614 B1 | 1/2001 | Anderson et al. | |
| 6,635,085 B1 * | 10/2003 | Caffey | A61F 2/2415 623/2.1 |

(Continued)

FOREIGN PATENT DOCUMENTS

| | | |
|---|---|---|
| SU | 1271508 A1 | 11/1986 |
| WO | WO 2007/100410 | 9/2007 |
| WO | WO 2010/079427 A1 | 7/2010 |

OTHER PUBLICATIONS

International Search Report and Written Opinion from corresponding international application No. PCT/IB2010/000049, dated Aug. 6, 2010, 14 pages.

(Continued)

*Primary Examiner* — Christian Sevilla
*Assistant Examiner* — Seema Mathew
(74) *Attorney, Agent, or Firm* — Cadwalader Wickersham & Taft LLP

(57) ABSTRACT

The present invention provides a modular prosthetic valve device having two or more device modules for percutaneous delivery unassembled at or near the valve implantation site and assembly at least in part using a self-assembly member, and a system and method of folding, delivering and assembling the device. The device modules may include a support structure and a valve module. The valve module has an unassembled, folded delivery configuration, and an unfolded, assembled (via the self-assembly member) working configuration. The valve module may be a single-piece leaflets substructure or a plurality of valve sections. The self-assembly member has a delivery configuration and may be reverted to a preset configuration for valve module assembly. The unassembled valve module may be rolled along its circumferential axis towards its height to a folded diameter equivalent to one rolled leaflet, providing a percutaneous valve device having a smaller delivery diameter than pre-assembled valve devices.

35 Claims, 8 Drawing Sheets

(56) References Cited

U.S. PATENT DOCUMENTS

| | | | |
|---|---|---|---|
| 6,733,525 B2* | 5/2004 | Yang et al. ............... 623/2.18 | |
| 6,893,460 B2 | 5/2005 | Spenser et al. | |
| 7,331,991 B2 | 2/2008 | Kheradvar et al. | |
| 7,927,369 B2* | 4/2011 | Andrieu ................ A61F 2/2418 | |
| | | | 623/2.13 |
| 8,377,115 B2* | 2/2013 | Thompson ............ A61F 2/2427 | |
| | | | 623/1.24 |
| 2003/0040792 A1 | 2/2003 | Gabbay | |
| 2004/0015230 A1 | 1/2004 | Moll et al. | |
| 2004/0122516 A1* | 6/2004 | Fogarty ............. A61B 17/0401 | |
| | | | 623/2.37 |
| 2005/0165479 A1 | 7/2005 | Drews et al. | |
| 2005/0283231 A1 | 12/2005 | Haug et al. | |
| 2006/0025855 A1 | 2/2006 | Lashinski et al. | |
| 2006/0195180 A1* | 8/2006 | Kheradvar ........... A61F 2/2418 | |
| | | | 623/2.11 |
| 2006/0265053 A1* | 11/2006 | Hunt .................... A61F 2/2412 | |
| | | | 623/1.24 |
| 2006/0287717 A1 | 12/2006 | Rowe et al. | |
| 2007/0016288 A1 | 1/2007 | Gurskis et al. | |
| 2007/0093887 A1* | 4/2007 | Case .................... A61F 2/2418 | |
| | | | 623/1.24 |
| 2007/0265701 A1 | 11/2007 | Gurskis et al. | |
| 2007/0288089 A1* | 12/2007 | Gurskis ................ A61F 2/2409 | |
| | | | 623/2.4 |
| 2008/0033541 A1 | 2/2008 | Gelbart et al. | |
| 2008/0161909 A1* | 7/2008 | Kheradvar ........... A61F 2/2418 | |
| | | | 623/2.11 |
| 2009/0005863 A1 | 1/2009 | Goetz et al. | |
| 2009/0062907 A1 | 3/2009 | Quijano et al. | |
| 2010/0179649 A1* | 7/2010 | Richter ................. A61F 2/2409 | |
| | | | 623/2.11 |
| 2010/0185275 A1* | 7/2010 | Richter ................. A61F 2/2412 | |
| | | | 623/2.11 |
| 2011/0137410 A1* | 6/2011 | Hacohen .............. A61F 2/2412 | |
| | | | 623/2.37 |
| 2012/0283820 A1* | 11/2012 | Tseng ................... A61F 2/2418 | |
| | | | 623/1.23 |
| 2015/0039084 A1* | 2/2015 | Levi .................... A61B 17/0057 | |
| | | | 623/2.38 |
| 2016/0030169 A1* | 2/2016 | Shahriari ............. A61F 2/2409 | |
| | | | 623/2.18 |
| 2016/0067038 A1* | 3/2016 | Park .................... A61F 2/2406 | |
| | | | 623/2.18 |

OTHER PUBLICATIONS

Singh, I.M. et al., "Percutaneous Treatment of Aortic Valve Stenosis," Cleve. Clin. J. Med. 75(11): 805-812 (Nov. 2008).

Piazza, N. et al., "Early and Persistent Intraventricular Conduction Abnormalities and Requirements for Pacemaking after Percutaneous Replacement of the Aortic Valve," JACC Cardiovascular Interventions 1(3): 310-316 (2008).

Piazza, N. et al., "Anatomy of the Aortic Valvar Complex and its Implications for Transcatheter Implantation of the Aortic Valve," Circ. Cardiovasc. Interventions 1:74-81 (2008).

Webb, J.G. et al., "Percutaneous Aortic Valve Implantation Retrograde from the Femoral Artery," Circulation 113: 842-850 (2006).

* cited by examiner

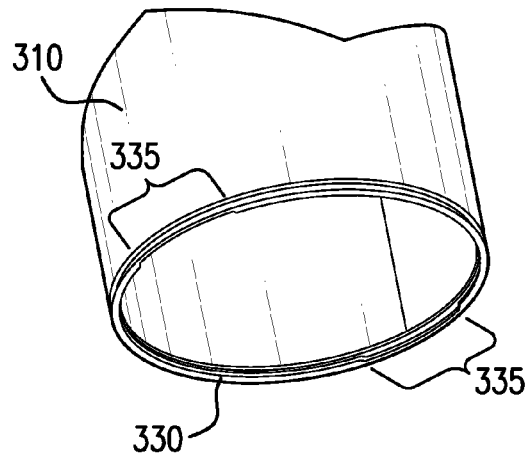
FIG.3A
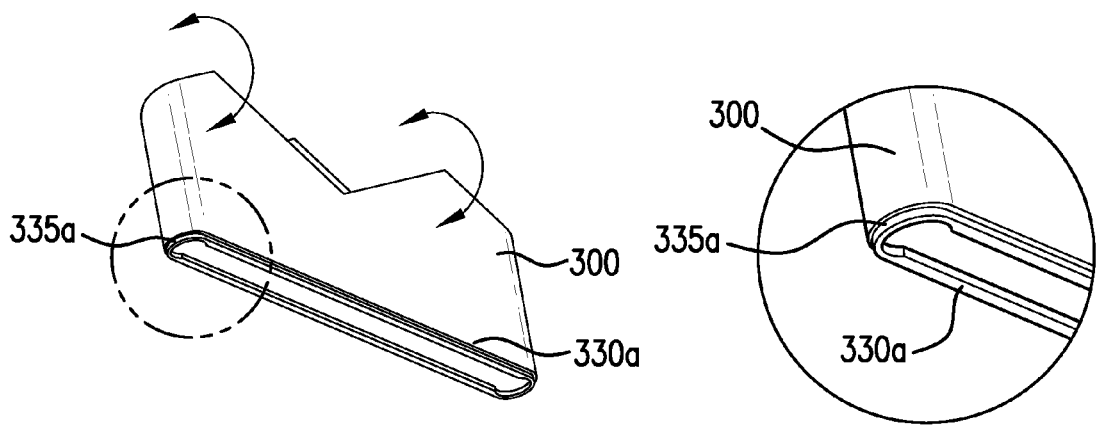
FIG.3B
FIG.3B'
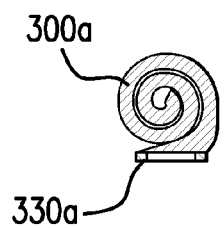
FIG.3C

SELF-ASSEMBLING MODULAR PERCUTANEOUS VALVE AND METHODS OF FOLDING, ASSEMBLY AND DELIVERY

FIELD OF INVENTION

The present invention relates to a multi-component, or modular, prosthetic valve device—a prosthetic valve capable of being delivered unassembled and assembled in the body—that at least in part is self-assembling, a self-assembly member, and a method of assembling a modular valve device using a self-assembly member. The present invention also relates to a method of folding and delivering such a modular valve device and assembling the device in the body using the self-assembly member. The modular nature of the valve device, design of the valve module and methods of folding the valve device provide a prosthetic percutaneous valve that is capable of having a smaller delivery diameter than fully assembled percutaneous valve devices. The present invention further relates to a system that includes the self-assembling modular valve device and a delivery device having a reduced diameter compared to a delivery device for a fully assembled percutaneous valve device.

BACKGROUND OF THE INVENTION

The human body contains a wide variety of natural valves, such as, for example, heart valves, esophageal and stomach valves, intestinal valves, and valves within the lymphatic system. Natural valves may degenerate for a variety of reasons, such as disease, age, and the like. A malfunctioning valve fails to maintain the bodily fluid flow in a single direction with minimal pressure loss. An example of a malfunctioning valve is a heart valve that may be either stenotic, i.e., the leaflets of the valve do not open fully, or regurgitant, i.e., the leaflets of the valve do not close properly. It is desirable to restore valve function to regain the proper functioning of the organ with which the valve is associated. For example, proper valve function in the heart ensures that blood flow is maintained in a single direction through a valve with minimal pressure loss, so that blood circulation and pressure can be maintained. Similarly, proper esophageal valve function ensures that acidic gastric secretions do not irritate or permanently damage the esophageal lining.

Several percutaneous prosthetic valve systems have been described. One example described in Andersen, et. al. (U.S. Pat. No. 5,411,552) comprises an expandable stent and a collapsible valve which is mounted onto the stent prior to deployment. The collapsible valve may be a biological valve or it may be made of synthetic material. The Anderson prosthetic valve is delivered and deployed using a balloon catheter which balloon is used to expand the valve-stent prosthesis to its final size. See also, U.S. Pat. No. 6,168,614 (Andersen, et al.) entitled "Valve Prosthesis for Implantation in the Body" and U.S. Pat. No. 5,840,081 (Andersen, et al.) entitled "System and Method for Implanting Cardiac Valves."

Spenser, et. al. (U.S. Pat. No. 6,893,460) describe another prosthetic valve device comprising a valve structure made of biological or synthetic material and a supporting structure, such as a stent. The Spenser prosthetic valve is a crimpable leafed-valve assembly consisting of a conduit having an inlet and an outlet, made of pliant material arranged to present collapsible walls at the outlet. The valve assembly is affixed to the support stent prior to deployment. The complete valve device is deployed at a target location within the body duct using a deploying means, such as a balloon catheter or a similar device.

Percutaneous implantation of prosthetic valves is safer, cheaper, and provides shorter patient recovery time than standard surgical procedures. However, current artificial percutaneous prosthetic valves have the disadvantage of being bulky, even when compressed for delivery. The problem with this bulkiness is that the delivery diameter of current valve devices and required diameter delivery systems combined with the anatomy through which the devices must be delivered can make delivery into the lumen problematic from the point of view of success rate, accuracy of deployment, and risk of complications. Specifically, delivery complications may arise due to the shape of the lumen, for example, the significant natural curve of the aortic arch and/or a tortuous iliac/femoral artery through which the catheter is introduced. Further, a larger diameter catheter tends to be less flexible than a smaller diameter catheter, especially when loaded with a bulky, inflexible device, and manipulating such a loaded catheter through a narrow vessel and in particular a curved vessel substantially raises the potential for damage to that vessel wall.

The delivery diameter of a prosthetic percutaneous valve is dependent in part on the way in which the valve is folded. There is a need in the art for a prosthetic valve device that may be folded in a manner that minimizes the diameter of the device for delivery, thereby minimizing complications and increasing the safety of the valve replacement procedure. A device that can be placed in the vessel without incurring further damage to the wall of the body lumen is highly desirable.

SUMMARY OF THE INVENTION

The present invention relates to a self-assembling, multi-component, or modular, percutaneous valve device comprising a plurality of device modules that may be delivered percutaneously as device modules that are either separate or fixedly connected to one another, but in either case are designed to be assembled in the body into a functioning valve device. The present invention provides valve modules that may assume shapes different from their functional valve shape that are particularly advantageous for delivery of the modules to the assembly site. The present invention also relates to a method of assembling a modular valve device using a self-assembly member, a method of folding the device modules for delivery, a modular valve device comprising device modules folded in a manner that minimizes the device diameter for delivery, and a method of delivering a modular valve device comprising folded device modules and a self-assembly member. The self-assembly member facilitates assembly of device modules limiting the requirement for remote operation, and makes the valve replacement procedure more efficient.

The modular prosthetic valve device comprises a self-assembly member and a plurality of device modules for delivery and assembly in vivo. From a functional perspective, the plurality of device modules may include a support structure and a valve module, which are designed to be assembled in the body, for example near the site of implantation, at the site of implantation, or at a location some distance from the site of implantation. The support structure provides the framework, or backbone, of the valve device, housing the valve module and holding it in place within the body lumen. The support structure preferably is expandable to a working configuration and is delivered in a compressed state. The valve module comprises the leaflets of the valve device and when assembled into a working configuration provides a conduit having a inlet end and an outlet end. The valve module may itself comprise one or more device modules, for example a one-piece structure that may be delivered unassembled and folded, or a plurality of valve sections that may be delivered unassembled and folded. The design of the prosthetic modular valve device, whether the valve module is fixedly connected to the support structure for delivery or not, permits folding the valve module in a manner that minimizes the diameter of the prosthetic device for delivery.

The device modules may be delivered to the desired location in the lumen within an appropriate delivery device such as a catheter and assembled in the body, for example in the aorta, in the ventricle, or at the site of implantation. Once the device modules are deployed from the delivery device into the lumen, they may be assembled to form a fully assembled valve device.

The self-assembly member preferably is attached to or threaded through the valve module, to permit efficient assembly of the valve module from its unassembled delivery configuration to its assembled working configuration. In some embodiments, the self-assembly member may concomitantly assist in unfolding the valve module from its delivery configuration. In some embodiments, the self-assembly member may enable attachment of the valve module to the support structure. In other embodiments, the self-assembly member may fixedly connect the valve module to the support structure during delivery. Like the device modules, the self-assembly member may have a delivery configuration and a working configuration. The working configuration of the self-assembly member may be a preset configuration which confers a functional shape to the valve module. The delivery configuration may be a configuration that facilitates delivery through narrow and tortuous vasculature. The self-assembly member may be triggered to revert to its preset configuration from its delivery configuration.

The system of the invention comprises a modular prosthetic valve device and a delivery device, within which the device modules are folded in a manner to minimize delivery diameter, for delivering the device modules to the desired location in the body.

The present invention also relates to a method of folding the valve module for delivery. The valve module in accordance with the invention may be unassembled and unfolded to a substantially flat configuration. From this unassembled, unfolded configuration, the valve module may be folded in a manner not possible for valve members of pre-assembled percutaneous valves in the art. That is, the unassembled valve module may be folded by rolling into a substantially cylindrical structure. For example, the unassembled valve module may be provided as a single layer structure that may be rolled along one axis, for example from base to apex, into a folded delivery configuration.

The present invention further relates to a method of delivering a modular valve device to a body lumen in need of a valve and a method of assembling the modular valve device within the body. The method of delivering the device modules to the desired location for assembly in the body includes percutaneously introducing a valve not as a whole, but in parts (modules), folded or rolled in a delivery device, and using a shape memory member, and optionally push-rods or guiding strings, to unfold, position and assemble the valve module after deployment from the delivery device.

Advantages that may be achieved by the present invention include that the percutaneous prosthetic valve system according to the invention reduces the bulkiness of the valve for delivery, compared to pre-assembled percutaneous valve devices, and thereby allows for increased flexibility and a reduced diameter of the delivery device. The present invention may also facilitate assembly of the modular valve device by requiring less remote manipulation. Also, the prosthetic valve device is minimally invasive and the method of percutaneous delivery reduces traumatic damage and minimizes procedure complications, thereby increasing the safety of the procedure and expanding the number of medical facilities equipped to perform percutaneous valve replacement procedures.

BRIEF DESCRIPTION OF THE DRAWINGS

FIGS. 3A-C illustrate how a leaflets-ring embodiment (FIG. 3A) of the valve module may be compressed to an unassembled state (FIG. 3B, FIG. 3B') and folded for delivery (FIG. 3C).

FIG. 5A schematically depicts the first and second self-assembly members in a preset configuration; FIG. 5B schematically depicts the first and second self-assembly members in delivery configuration with a folded, unassembled leaflets substructure; FIG. 5C schematically depicts the assembled valve module.

FIG. 6A schematically depicts the self-assembly member in a preset configuration; FIG. 6B schematically depicts the self-assembly member in a delivery configuration.

FIG. 8A illustrates guiding strings attached to the masts of the self-assembly embodiment of FIG. 6A; FIG. 8B illustrates guiding strings attached to the commissure points of the valve module embodiment of FIG. 7.

DETAILED DESCRIPTION OF THE INVENTION

Figure 1A:
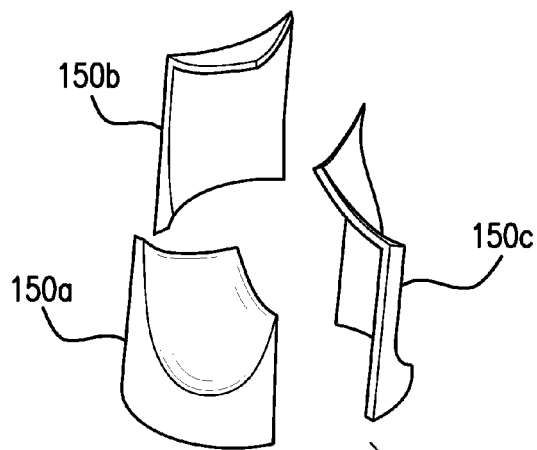
FIGS. 1A and 1B illustrate a valve module that includes 3 valve sections unassembled (FIG. 1A) and assembled into a working configuration (FIG. 1B).

The present invention provides a self-assembling modular prosthetic valve device comprising a self-assembly member, and method for assembling an implantable modular percutaneous prosthetic valve device in the body. The invention provides a self-assembly member that effects a change in the relative form of a valve module of the modular valve device, in particular from an unassembled configuration to an assembled configuration. A self-assembly member may also provide a means for assembling and/or connecting the valve module and the support structure. The unassembled valve module may be folded in a manner that minimizes its diameter for delivery, and therefore also minimizes the required diameter of the delivery device. The self-assembly member may also effect unfolding of the valve module from its delivery configuration. Thus, the present invention further provides a modular valve device comprising a folded valve module, a method of folding a valve module for percutaneous delivery, and a method of delivering a modular valve device that includes transforming the valve module from its folded, unassembled delivery configuration into its assembled working configuration. The modular prosthetic valve device facilitates safe delivery into a lumen without the need for invasive surgery.

The percutaneous modular valve device of the invention comprises a self-assembly member and a plurality of device modules, such as a support structure and a valve module. The valve module may comprise one device module, i.e., a valve component, or it may comprise a plurality of device modules, i.e., a plurality of valve sections that may be assembled into a valve assembly. In accordance with the invention, the device modules may be delivered sequentially and assembled in the body via the self-assembly member. In particular, the self-assembly member may assist assembly of the valve module from a folded delivery configuration into a 3-dimensional working configuration. Preferably, the self-assembly member may be attached to or threaded through the unassembled valve modules prior to folding for delivery, and thereby may assist both in the unfolding and assembly of the valve modules. As used herein, the phrase "attached to" is intended to encompass "threaded through" in the context of the self-assembly member attached to a valve module (assembled or unassembled), such as along the base line or elsewhere on the valve module.

One embodiment of the valve module is a single-piece valve module that may be folded into a delivery configuration and delivered apart from the support structure, and then unfolded and assembled via a self-assembly member into a valve component having a conduit, i.e., working configuration, and then combined with the support structure. In one aspect of this embodiment, the single-piece valve module that in an unassembled state may be a leaflets substructure that comprises a row of contiguous leaflets, which may be folded—for example by rolling along an axis—into a delivery configuration. To form the assembled valve component (i.e., the working configuration), the row of leaflets may be arranged in a 3-dimensional structure wherein the two ends of the leaflets substructure meet and are connected. The self-assembly member may be attached to the leaflets substructure to effect assembly thereof. The self-assembly member may assemble the leaflets substructure into a valve component by reverting to a preset configuration, moving the attached leaflet substructure with it to arrange the leaflet substructure to form the valve component—an assembled, working configuration having a conduit.

In another aspect of this embodiment, the single-piece valve module in its unassembled state may be a ring of leaflets (leaflets-ring) that is squashed to a two-ply, substantially flat configuration for folding, e.g., rolling along a single axis, for example base to apex, into a delivery configuration. In this aspect of the embodiment, the self-assembly member may have a compressed delivery configuration and may revert to a pre-set configuration that is a ring commensurate in diameter with the leaflets-ring to which it is attached to assemble the leaflets-ring into an assembled, working configuration having a conduit.

In another embodiment, the valve module is a single-piece valve module, similar to either aspect described above, that may be folded into a delivery configuration and delivered to the body lumen fixedly connected to the support structure, rather than apart from the support structure, and then unfolded and assembled via a self-assembly member into a valve component having a conduit (working configuration), and assembled with the support structure to form a fully assembled valve device.

In yet another embodiment, the valve module comprises a plurality of valve sections that, in an unassembled configuration, may be folded individually or together into a delivery configuration, and then unfolded and assembled to form a valve assembly (working configuration) using the self-assembly member. The valve sections may be partially connected by way of the self-assembly member, which may be attached to each valve section. The valve assembly may be combined with the support structure to form an assembled valve device. The self-assembly member may revert to a preset configuration, moving the attached valve sections with it, so that the valve sections are arranged to form the valve assembly.

The plurality of valve sections are shaped such that they may fit together to form the valve assembly that, like the above-described valve component, opens and closes to permit one-way fluid flow and functions in a manner that closely matches the physiological action of a normally functioning native valve.

The modular valve device may still further comprise valve sections that are delivered folded individually or together, and then unfolded and assembled into a valve assembly using the self-assembly member and implanted without a support structure. Thus, in this embodiment, the valve device comprises a plurality of valve sections and a self-assembly member attached to each valve section thereby partially connecting the valve sections. The self-assembly member may operate to arrange the valve sections to form a valve assembly in a manner similar to that described above.

As used herein, "assembled" means that the valve assembly, valve component, or valve device is in a working configuration (e.g., substantially tubular, rather than flat, compressed or separated device modules), but the modules are not necessarily locked together. Thus, the "unassembled" valve module may be folded for delivery (delivery configuration) or unfolded and ready for assembly. The "unassembled" single-piece valve component may include a leaflets substructure—a one-layer, substantially flat structure having a first end and a second end, which may be assembled into a valve component (working configuration having a conduit) by arranging the first and second ends to meet to form a ring. Alternatively, the single-piece valve component may include a leaflets-ring that unassembled is a two-ply substantially flat structure, and that may be popped open to form the assembled valve component. Similarly, as set forth above, the "unassembled" valve assembly includes a plurality of valve sections, which may be attached to one another in tandem, e.g., laid out in a series rather than arranged in a ring, to optimize folding of the modules for delivery. Alternatively, the valve sections may be unattached and delivered separately. In these and other embodiments of the valve module described herein, the unassembled configuration provides a useful shape for folding the valve module into a low profile delivery configuration.

The device module(s) that make up the valve module of the invention are provided in two configurations: unassembled and assembled. The unassembled configuration provides a particular advantage for delivering the valve module. Because of the unassembled configuration, the valve modules of the invention may be folded to a delivery configuration, which minimizes the diameter of the valve modules for delivery. The assembled configuration may also be referred to as a working configuration, where the valve module is substantially tubular and provides a conduit with the leaflets in place.

The self-assembly member may be a wire, a band, or a strip, or a plurality of wires or bands or strips. If a wire, the self-assembly member may have a round or rectangular (e.g., square) cross-section. The self-assembly member has a delivery configuration that permits a small diameter delivery profile and a preset configuration, which may be any pre-selected shape appropriate for assembling the valve module or valve device. The self-assembly member may be manufactured from any of a variety of materials, such as, for example, a shape-memory alloy, cobalt chromium, or a polymeric deformable plastic. In one embodiment, the self-assembly member comprises a shape-memory metal or alloy, pre-conditioned to revert to the preset configuration. In one aspect of this embodiment, the self-assembly member is a shape-memory alloy wire.

The preset configuration may be referred to as a first configuration (e.g., a relaxed state) and the delivery configuration may be referred to as a second configuration (e.g., an unrelaxed, or restrained state). The self-assembly member may be triggered to revert to the preset configuration by, for example, a change in temperature (heating or cooling), an electrical current, or release from a geometric restriction. In some embodiments, the delivery device, or a shaft or lumen within the delivery device, may restrain the self-assembly member in a delivery configuration, and the trigger may be a release from the restraint. As used herein, "preset configuration" or "first configuration" with respect to self-assembly members is not limited to shape-memory structures. By "preset configuration" and "first configuration" is meant the pre-selected shape that the self-assembly member is triggered to assume or revert to after deployment from the delivery device. The shape memory alloy allows the self-assembly member to be thermo-mechanically pre-conditioned into a preselected shape (pre-set configuration), so that it may be delivered in for example a relatively straight, but axially flexible second configuration and then be triggered to revert to the thermo-mechanically preset first configuration. Reversion of a shape memory self-assembly member to its first configuration may be triggered, for example by a temperature step or by release from geometrical restriction. The temperature step may be effected by changing the temperature in the environment around the self-assembly member, for example by hot fluid, cool fluid, body heat, or passing electrical current through a wire to generate resistive heat. Any shape memory alloy may be used to make the shape memory self-assembly member. In specific embodiments, the shape memory alloy used is NiTi (e.g., NiTinol), CuZnAl, CuAlNi, or a mixture thereof (see, e.g., SHAPE MEMORY MATERIALS, edited by Otsuka and Wayman, Cambridge University Press; October 1999 and SHAPE MEMORY ALLOYS, edited by Youyi and Otsuka, International Academic Publishers, June 1998).

The pre-selected shape of the self-assembly member may be a shape consistent with the shape of the working configuration of the valve module, e.g., a substantially circular, elliptical, multi-lobular or D-shape, or another shape useful to arrange, support or lock one or more device modules. The self-assembly member may include axially oriented appendages (posts or masts)—i.e., oriented along the longitudinal axis of the valve in a preset configuration—that may be used to assemble or connect the valve module and support structure into an assembled valve device or provide commissural support for the valve module. Alternatively, the self-assembly member may include a first and second self-assembly member. The second self-assembly member may include posts or masts, which may interact with the support structure to engage the valve module and support structure or which may provide commissural support to the valve module. Thus, for example, in one embodiment the first self-assembly member in its preset configuration may be a ring to assemble the valve module into a circular form and the second self-assembly member in its preset configuration may include axially oriented masts to support the valve commissures. Push-rods may be used to position the self-assembly member and/or valve module to assist in unfurling and/or assembling the valve module. Push-rods may also be used to assist in positioning the valve module for combination with the support structure. In some embodiments, the masts may serve as push-rods or extensions of push-rods. In one embodiment, push-rods may extend out the proximal end of the delivery device and be manipulated by the operator therefrom. In another embodiment, the push-rods may be integral to the delivery system. Alternatively, guiding strings or pull wires may be used to guide the position of the valve module during assembly and/or to assist combining the valve module and the support structure.

The valve module may be manufactured from suitable materials, such as polymers, metals or biological material, such as pericardium. The selection of material, structure and method of manufacturing preferably is made to facilitate the function, the durability and the biocompatibility of the valve.

The support structure may be manufactured from a biocompatible material that is sufficiently durable that the structure may support the valve component or valve assembly while maintaining the device's position in the lumen. The support structure material also is compatible with delivery of the support structure in a compressed state and expansion of the compressed support structure upon deployment in the lumen. In one embodiment of the present invention the support structure may be manufactured from stainless steel or a shape memory alloy, such as, for example, Nitinol. In another embodiment, it may be made of amorphous metal of suitable atomic composition. Other further embodiments of the support structure may be manufactured from similar biocompatible materials known in the art. In one embodiment, the support structure is annular, but it may be provided in other shapes too, depending on the cross-sectional shape of the lumen at the location the valve is to be implanted. One non-limiting example of an appropriate support structure is a stent. The support structure preferably is expandable, so that it may be delivered compressed (unexpanded), and then expanded for implantation and assembly of the valve device. The stent, or any other support structure, may, for example, be self-expanding or balloon-expandable. Other similar support structures are known in the art and are interchangeable with a stent in accordance with the invention.

Further details regarding the structure, function and various uses of some embodiments of the modular valve device are set forth in ¶¶37-47, 60-62, 65-82 and FIGS. 1-6c of co-pending U.S. patent application Ser. No. 12/686,335 (modular), filed on date even herewith, which is incorporated herein by reference in its entirety. For example, the devices, systems and methods are particularly adapted for use in percutaneous aortic valve replacement, but may also find use as replacements for other cardiac valves, such as, e.g., pulmonic, mitral and tricuspid valves, as well as valves in the peripheral vasculature or in other bodily lumens, such as the alimentary canal, e.g., esophagus; lymph ducts; the biliary duct; and any other lumens having valves requiring replacement or needing valve implantation.

The manner in which a percutaneous valve device is folded affects the diameter of the prosthetic valve during delivery and the required diameter of the delivery device. The structure of the valve modules of the invention permits folding in a manner not available for current percutaneous prosthetic valve devices. For current percutaneous prosthetic valve device, the diameter of the device during delivery is rather large and cannot be adjusted significantly by folding the valve in a different manner. By contrast, the modular valve of the invention provides a valve module that may be folded into a delivery configuration from an unassembled configuration, i.e., it is not folded from a 3-dimensional working configuration. The unassembled, unfolded valve module of the invention may be laid out substantially flat (e.g., "2-dimensional"), so that the leaflets of the valve device are arranged in a series or contiguously in a row for folding, and therefore may be folded or rolled from a substantially flat configuration into its delivery configuration, for example from base to apex.

Specifically, the valve assembly in an unassembled, unfolded form comprises a plurality of valve sections, each having a height (base-apex), which is in the general direction of the longitudinal axis of the assembled valve device (and body lumen)—i.e., axially, and a circumferential axis, which is in the general direction of the circumference of the valve assembly. Similarly, a valve component in an unassembled, unfolded form may comprise a leaflets substructure having a generally rectangular or trapezoidal form, when laid out substantially flat, which comprises a row of contiguous leaflets. The leaflets substructure has a length (or circumferential axis)—which includes the circumferential axis of each leaflet, and a width (or height) extending between the base and the apex of the row of leaflets. The length of the leaflets substructure becomes the circumference of the valve component once assembled (similar to the combined circumferential axes of the valve sections of a valve assembly). Thus, in any of these embodiments, the unassembled valve module may be rolled in the direction of its height or in the direction of its circumferential axis without need for further folding of the valve module. It may be desirable to roll the valve modules in the direction of its height, that is, base to apex. The single-piece valve component that is a preconnected ring of leaflets (leaflets-ring), when squashed to a substantially flat unassembled configuration also has a length (or circumferential axis) and a width (or height) and may be rolled in the direction of its height. Folding the unassembled valve modules in this manner, combined with the separate compressed support structure, minimizes the diameter of the valve device for delivery.

The present invention also provides a method of delivering a modular valve device to a body lumen in need of a valve and a method of assembling the modular valve device within a lumen.

The method of delivering the modular valve device includes delivering the device unassembled in a delivery device, for example a catheter. The two or more device modules may be provided pre-loaded in a delivery device such as catheter or other similar device known in the art, or may be loaded into the delivery device after the delivery device is inserted into the body lumen. The support structure and valve module (e.g., leaflets substructure or valve sections) may be loaded in tandem into the catheter. Alternatively, the support structure may be loaded into the catheter first and delivered, then, for example, the valve sections may be loaded in tandem into the catheter and delivered into the support structure and the complete device assembled. The self-assembly member may be bundled with the folded valve module and compressed support structure for delivery in the delivery device. The methods described herein enable percutaneous delivery of a prosthetic artificial valve through a smaller diameter lumen than currently required for percutaneous artificial valves in the art by delivering the valve device as unassembled device modules and assembling the valve modules in the body. In alternative embodiments, a modular heart valve may be assembled in the left ventricle. In still alternative embodiments, the modular valve device may be assembled in whole or in part within the delivery device. For example, the delivery device may include an assembly room, a portion of the delivery device in which there is sufficient space to trigger the self-assembly member and assemble the valve module or even combine the valve module and support structure.

The method of assembling the device modules includes triggering the self-assembly member, attached to or threaded through device modules, to assume a preset configuration that arranges the device modules in the three-dimensional shape of the valve device (or valve module), and in some embodiments where the self-assembly member does not lock the device modules together, the method further includes attaching the device modules to one another using locking mechanisms. The self-assembly member permits assembly of the valve module without the need for remote manipulation, or minimizing the need for remote manipulation. In one embodiment, a second self-assembly member may be used to support the valve commissures. The second self-assembly member may be triggered to revert to its preset configuration simultaneously with the first self-assembly member or separately from the first self-assembly member. In another embodiment, a second self-assembly member may be used to combine the valve module and the support structure into the assembled valve device. In another embodiment, guiding strings or push-rods may be used to guide the assembly process. In yet another embodiment, pull wires may be used to assist in positioning the self-assembled valve assembly within the support structure and to assemble the support structure and valve module into the assembled valve device. The guiding strings may be manipulated from the proximal end of the catheter.

The aforementioned embodiments, as well as other embodiments, delivery methods, different designs and different types of devices are discussed and explained below with reference to the accompanying drawings. Note that the drawings are provided as an exemplary understanding of the present invention and to schematically illustrate particular embodiments of the present invention. The skilled person will readily recognize other similar examples equally within the scope of the invention. The drawings are not intended to limit the scope of the present invention defined in the appended claims.

Figure 1B:
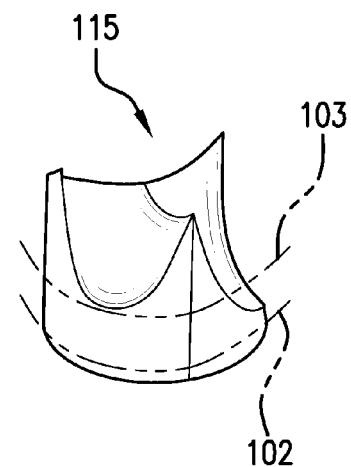
Figure 1C:
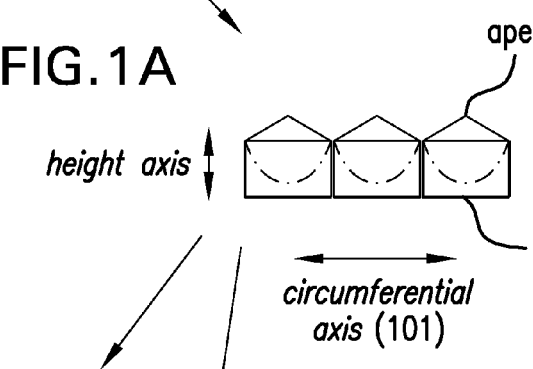
FIGS. 1C, 1C' and 1D illustrate ways of folding valve sections into delivery configurations.
Figure 1C:
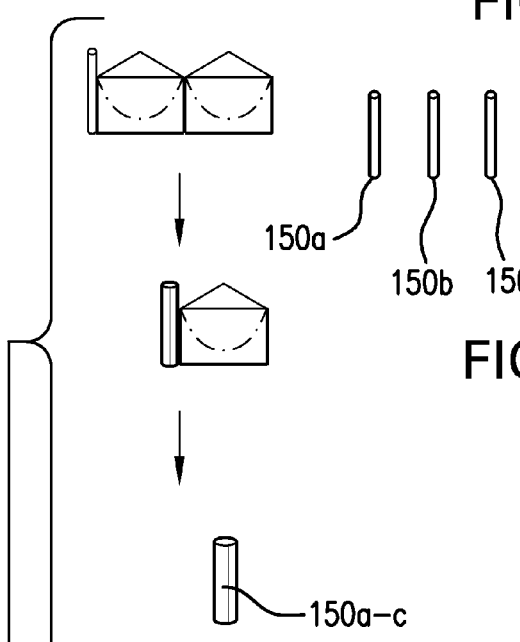

In one embodiment, the modular valve device may include four device modules: three valve sections 150a-150c depicted in FIG. 1A and a support structure (not shown). The valve sections 150a-150c are designed to fit together to form a valve assembly 115, as illustrated in FIG. 1B. In use, the valve assembly operates much as the folds of tissue in a native valve. The valve sections, e.g., 150a-c, that make up a valve assembly 115 may be folded for delivery in several ways. Different possible ways of folding valve sections are illustrated in FIGS. 1C and 1C' (side to side) and 1D (apex to base), which depict the valve sections schematically and without a self-assembly member.

Figure 1D:
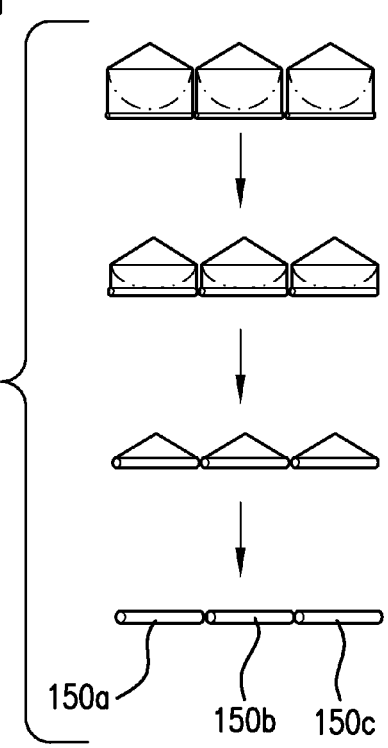

Each valve section has a height axis, extending between the base and apex, and a circumferential axis (101), the axis of the valve section width. Combined, the circumferential axes of the valve sections equal the circumference of the valve assembly. FIG. 1C illustrates one way of folding three valve sections by rolling along their height axes in the direction of their width (circumferential axes), which results in a single folded, unassembled valve module (generally cylindrical in shape) having a diameter that includes all three folded valve sections and a length equivalent to the height of the valve sections. In an alternative embodiment, illustrated in FIG. 1C', the valve sections may be separately rolled along their height axes in the direction of their circumferential axes 101, which results in three folded, unassembled device components (generally cylindrical in shape) each having a diameter smaller than that achieved by the method shown in FIG. 1C. FIG. 1D illustrates one way of folding three valve sections by rolling along their adjacent, parallel circumferential axes 101 in the direction of their height, base to apex, i.e., in the general direction of the longitudinal axis of the valve, which results in a folded unassembled valve module (generally cylindrical in shape) having a diameter of only one folded valve section, which is smaller than the diameter of FIG. 1C, and a length equivalent to the sum of the widths (circumferential axes) of the valve sections, because the valve sections are either attached together, for example, via the self-assembly member. In an alternative embodiment (not shown), three valve sections may be rolled separately along their circumferential axes 101 in the direction of their height, i.e., in the general direction of the longitudinal axis of the valve, which results in three folded unassembled device modules (generally cylindrical in shape), each having the same diameter as FIG. 1D. FIG. 1D illustrates rolling valve leaflets from base to apex, but valve leaflets alternatively may be rolled from apex to base into a delivery configuration.

In accordance with the invention, to minimize the diameter of the valve assembly of the invention when folded for delivery—and thereby minimize the diameter of the delivery device, each of the modules of the valve assembly may be rolled in the direction of their height, as illustrated by FIG. 1D. The valve sections may then be delivered in sequence as a train of modules—in tandem (tethered together) or separately—and then unfurled and assembled. Valve sections rolled in the direction of their circumferential axis, as depicted in FIG. 1C', also may be delivered in sequence as a train of modules, providing a minimized diameter for delivery, and then unfurled and assembled. FIGS. 1C, 1C', and 1D show how three valve sections may be folded, however the design of the prosthetic valve device of the invention permits a valve assembly comprising fewer or more than three valve sections to be folded in a similar manner, so as to have the same minimized delivery diameter. The diameter of the folded valve sections rolled along the circumferential axis in the direction of the height axis (as shown in FIG. 1D) or rolled separately along the height axis in the direction of the circumferential axis (as shown in FIG. 1C') will be equivalent to a single rolled leaflet irrespective of the number of leaflets that the valve assembly has.

A self-assembly member may be used to assemble the valve sections 150a-150c to form a valve assembly 115 in accordance with the invention. The self-assembly member may be attached to the series of valve sections 150a-150c at the base line 102, the commissures attachment height line 103, or both the base line and commissures attachment height line 102, 103 (represented as dotted lines in FIG. 1B), at the tip of the apex (not shown) or at another point along the height (base-to-apex) axis. The self-assembly member may be used to assemble the valve sections 150a-150c to yield the valve assembly 115. Optionally, the valve sections 150a-150c may be pre-fitted with and tethered by pull wires or strings (not shown) to tether the valve sections 150a-150c together for delivery purposes, so that they may be delivered through the lumen in tandem. In ordinary use, a self-assembly member comprising shape memory alloy will fairly quickly assemble the valve sections as it reverts to its preset shape, increasing the efficiency of assembling the valve device.

Figure 2A:
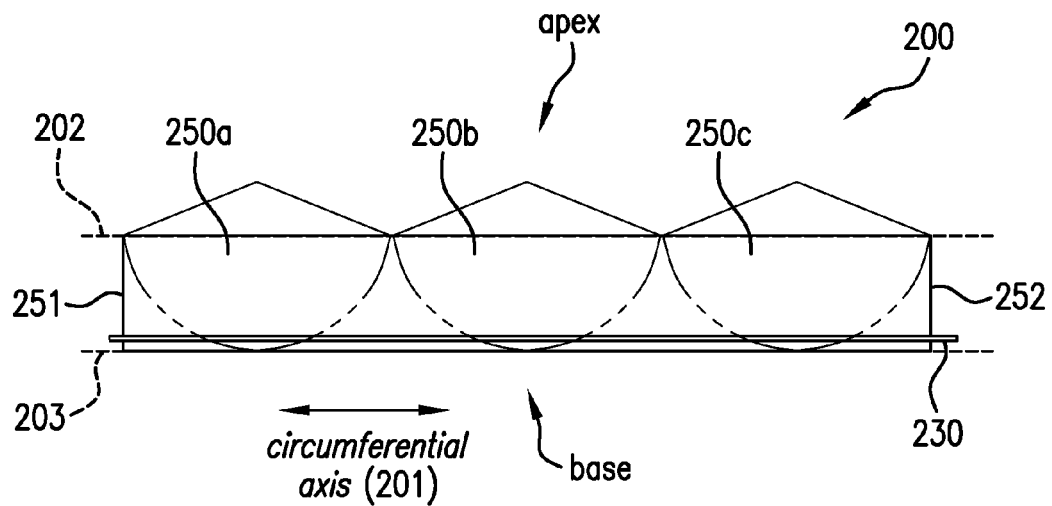
FIGS. 2A-2C illustrate a leaflets substructure prior to folding and delivery (FIG. 2A), one way of folding a leaflets substructure for delivery (FIG. 2B, a delivery configuration), and a leaflets substructure unfurled and assembled using a self-assembly member into a valve component (FIG. 2C, a working configuration).
Figure 2B:
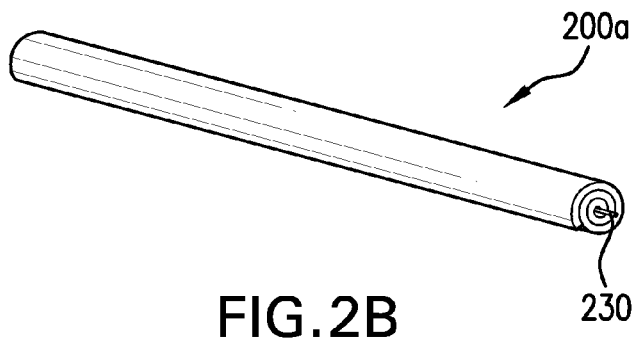
Figure 2C:
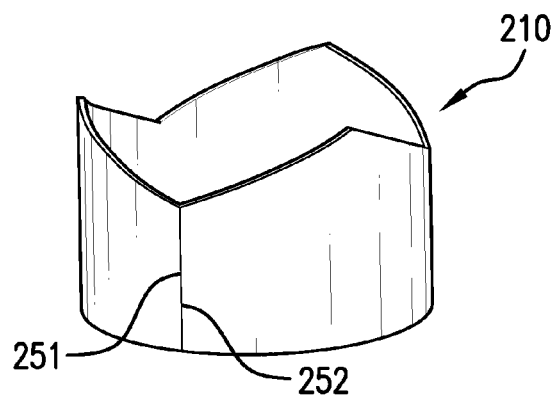

FIGS. 2A-2C depict another embodiment of a valve module: a single-piece valve module (valve component) that, unassembled, may comprise a leaflets substructure 200, which may be folded in a manner that minimizes the delivery diameter, i.e., its delivery configuration. Before loading the leaflets substructure 200 into the delivery system, it may be laid out in an unfolded, unassembled, substantially flat and generally rectangular or trapezoidal form, having a height axis, extending between the base and the apex (i.e., along the longitudinal axis of the assembled valve device), and a circumferential axis 201 as illustrated in FIG. 2A. The circumferential axis of the leaflets substructure is commensurate with the circumference of the assembled valve component. Before loading into the delivery device, the leaflets substructure may be rolled along its circumferential axis, either from base to apex, as illustrated in FIG. 2B, or apex to base, the first and second ends 251, 252 of the leaflets substructure 200 forming the ends of the folded leaflets substructure 200a. After deployment of the rolled or furled leaflets substructure from the delivery device, the leaflets may be unfurled to form the 3-dimensional structure of the valve component, as illustrated in FIG. 2C, as assisted by the self-assembly member of the invention, and/or by pull wires (not shown). The self-assembly member 230, in this embodiment a wire, may be preset to form a substantially circular shape, bringing the two ends 251, 252 of the leaflets substructure together, as illustrated in FIG. 2C. In the embodiment depicted in FIGS. 2A-2C, the leaflets substructure 200 has three leaflets 250a-250c, but the self-assembly member 230 may be used with leaflets substructures having 2 or more leaflets.

In this embodiment, the self-assembly member 230 may be attached at the base line 202 of the leaflets substructure, as depicted in FIG. 2A, to assist in assembling the valve component. However, in other embodiments, the self-assembly member may be attached or threaded through the leaflets substructure at the commissures attachment height line 203 of the leaflets substructure 200, and in still other embodiments the self-assembly member may be attached at both the base line and the commissures attachment height line 202, 203 (each represented as a horizontal dotted line parallel to the circumferential axis in FIG. 2A), or other circumferential line along the base-apex axis, to assist in assembling the valve component by, for example, contributing to the unfurling of the leaflets substructure 200 and the forming of the valve component shape. Where the self-assembly member 230 is attached at the base line 202 and the leaflets substructure 200 may be rolled along the circumferential axis from base to apex, and the self-assembly member 230 may be bundled in the folded leaflets substructure 200a as illustrated in FIG. 2B. Where the self-assembly member 230 is attached at the base line 202 and the leaflets substructure 200 is rolled along the circumferential axis from apex to base, the self-assembly member 230 may be bundled along-side the folded leaflets substructure 200a (as shown for another embodiment in FIG. 5B). Where the leaflets substructure is rolled along the height axis (not shown), the self-assembly member may have a delivery configuration other than a straight wire. The self-assembly member may be triggered to revert to its preset configuration after the leaflets substructure is deployed from the delivery device. Locking mechanisms may be used to lock the first end 251 to the second end 252 of the leaflet substructure 200 together after the three-dimensional valve module is formed, as described further below.

Another embodiment of a single-piece valve module comprises a ring of valve leaflets (leaflets-ring), e.g., similar to the leaflets substructure, but with the ends connected during delivery—i.e., a substantially tubular structure, as illustrated in FIGS. 3A-C. FIG. 3A illustrates the leaflets-ring 310 in its deployed state, i.e., its 3-dimensional working configuration forming a conduit. A self-assembly member 330 may be attached to the base of the leaflets-ring 310. The self-assembly member 330 may have a preset first configuration similar in shape to the deployed (assembled) leaflets-ring 310. As depicted in FIGS. 3B and 3C, the leaflets-ring may have an unassembled configuration and a folded delivery configuration, respectively. The self-assembly member 330 may be thermo-mechanically preset to the first configuration, but converted to is second configuration for folding and delivery of the valve module. Alternatively, the self-assembly member 330 may be geometrically constrained in the second configuration for delivery. In this embodiment, the self-assembly member 330 includes two flexure regions 335 having a different property than the rest of the self-assembly member, such that in their second configuration, these flexure portions 335a form a bend, as illustrated in FIG. 3B', so that the self-assembly member 330a in its delivery configuration may be substantially linear. The different property of the flexure portion 335 of self-assembly member that achieves the bend may include, for example, the thickness of the material, the composition of the material, or, where the self-assembly member is made of a shape memory alloy, how the material is thermo-mechanically preset. FIG. 3B schematically shows the unassembled leaflets-ring 300 squashed into a two-layer, substantially flat, unassembled configuration, and the self-assembly member 330a/335a in its delivery configuration. FIG. 3B" depicts an enlarged view of the self-assembly member 330a and the flexure portion of the self-assembly member 335a in their delivery configuration. When the leaflets-ring 300 is in its unassembled configuration as shown in FIGS. 3B and 3B", the self-assembly member 300 may be in a form that permits it to be folded into a low profile delivery configuration. FIG. 3C shows the folded leaflets-ring 310a in cross-section, rolled on a single circumferential axis in the direction of its height axis, from apex to base (as indicated by the arrows in FIG. 3B), to a low profile delivery configuration. By rolling the leaflets-ring along the circumferential axis in this direction, the self assembly member 330a in its delivery configuration is on the outside of the resultant cylindrical delivery form. In its deployed, working configuration, the leaflets-ring 310 may be combined with a support structure to form an assembled valve device.

Use of a second self-assembly member is compatible with this embodiment, and may include masts or posts or may be a second ring, located at another position on the valve component. Like the embodiments depicted in FIGS. 1C, 1C, 1D and 2B, this embodiment also presents an advantage over pre-assembled (non-modular) percutaneous prosthetic valve devices, because a smaller delivery diameter is provided. In addition, the valve component's altered (unassembled) shape facilitates rolling or folding of the component in ways not known in the prior art.

Figure 4A:
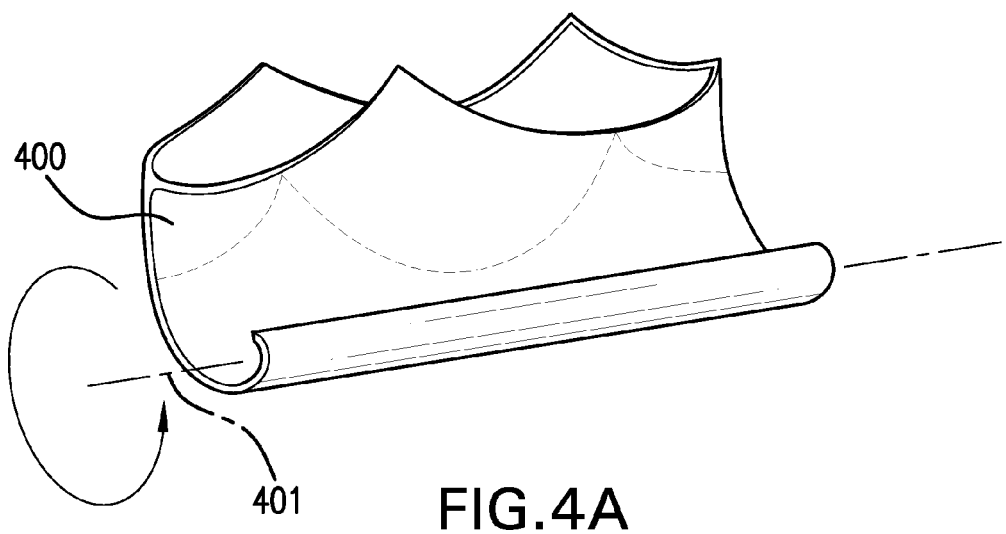
FIGS. 4A-B illustrate two directions in which an unassembled leaflets-ring embodiment of a valve module may be rolled.
Figure 4B:
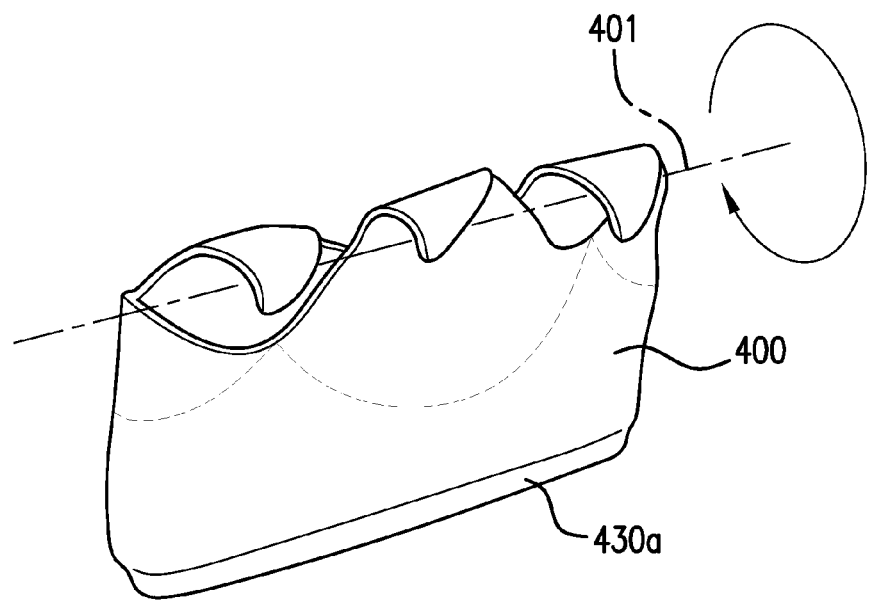

In this embodiment, the valve module may be folded into its delivery configuration as follows: the leaflets-ring be rolled along its circumferential axis in the direction of its height, from base to apex or apex to base, resulting generally cylindrical shape. FIGS. 4A-B illustrate two directions in which the unassembled leaflets-ring 400 embodiment of the valve module may be folded. In FIG. 4A, the unassembled leaflets-ring 400, that includes a self-assembly member in a delivery configuration (not shown), is rolled along its circumferential axis 401 from base to apex (rolling direction indicated by the arrow). In FIG. 4B, the unassembled leaflets-ring 400, that includes a self-assembly member in a delivery configuration 430a, is rolled along its circumferential axis 401 from apex to base (rolling direction indicated by the arrow). The folded leaflets-ring 400a, 300a may be unfolded by the action of the self-assembly member automatically reverting to its pre-set configuration or by use of pull wires. In the latter embodiment, for example, one or more pull wires may be attached to the apical portion of the leaflets, folded with the leaflets into the delivery configuration, and pulled to unfold the leaflets. Push-rods may be used in conjunction with the pull wires. In this and other embodiments, push-rods may be, for example, stiff wires or tubular structures.

Percutaneous valve devices in the art cannot be folded as described, because they are delivered pre-assembled or are not designed to be disassembled for folding in this manner. The leaflets of the valve devices in the prior art are required to be arranged in a circle, rather than in a series or row as in the present invention, and therefore a single leaflet diameter folding is not possible. Moreover, pre-assembled prosthetic valve devices in the art either have a device frame that is rigid or otherwise contributes to the delivery diameter of the device because the valve member is crimped and assembled within the device frame prior to percutaneous delivery. Similarly, the methods of folding the unassembled valve module illustrated in FIGS. 3C, 4A, and 4B present an advantage over percutaneous prosthetic valve devices in the art, because the leaflets-ring embodiment of the valve module is designed for rapid assembly from an unassembled form that permits folding into a low profile delivery configuration.

Figure 5A:
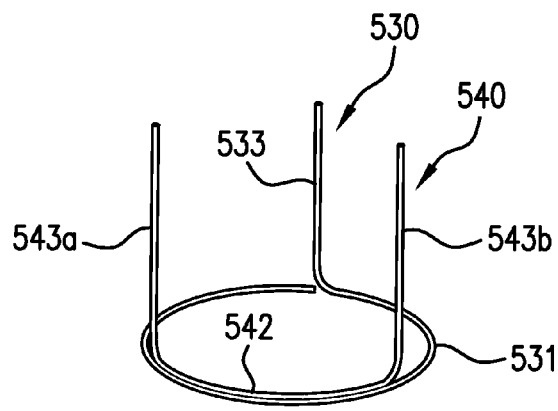
FIGS. 5A-5C illustrate one embodiment of a self-assembly member for use with a valve module, that includes a first self-assembly member and a second self-assembly member.
Figure 5B:
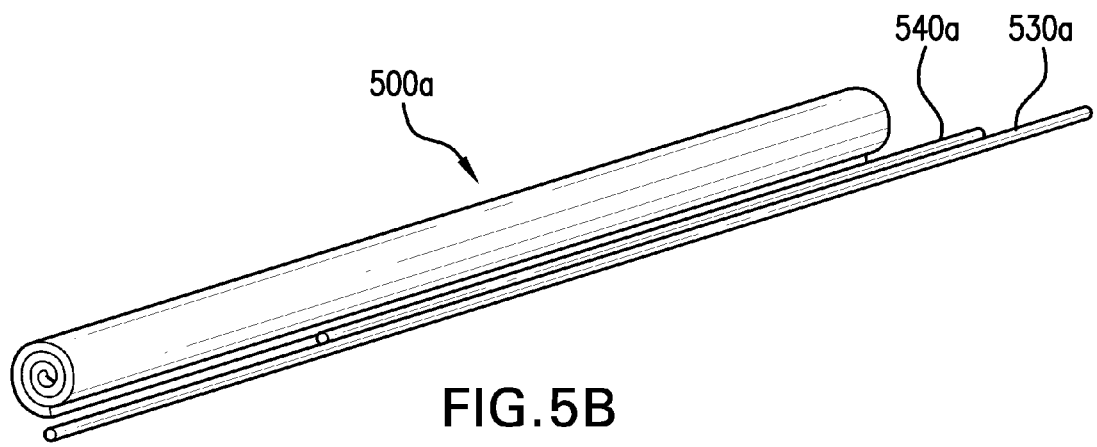
Figure 5C:
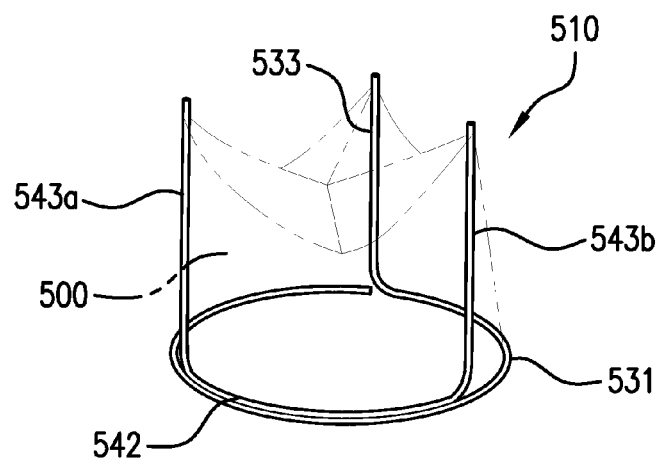

An embodiment of a self-assembly member, comprising a first self-assembly member and a second self-assembly member, is illustrated in its preset configuration in FIG. 5A. FIGS. 5B-5C illustrate how this embodiment of the self-assembly member may be delivered with a leaflets substructure and used to assemble the leaflets substructure. As shown in FIG. 5A the first self-assembly member 530 includes a main ring 531 and a mast 533, and a second self-assembly member 540 includes a base portion 542 aligned with and attached to the first assembly member and two masts 543a, 543b. In this embodiment, the second self-assembly member 540 is welded to the first self-assembly member 530, both of which may be manufactured from a shape-memory alloy, for example Nitinol. Other ways of connecting the first and second self-assembly members are also applicable and within the skill in the art. Alternatively, the first and second self-assembly members may not be connected. In both the delivery configuration and the preset configuration, the masts 533, 543a, 543b are oriented axially. In the preset configuration, the masts 533, 543a, 543b are oriented parallel to one another and perpendicular to the ring 531 and base portion, for example extending in the distal direction from the ring 531 and base portion 542 as shown in FIG. 5A, and in use may provide commissural support to the valve module material. In alternative embodiments mast 533 may extend proximally. In another alternative embodiment, masts 543a and 543b may extend proximally. In a further alternative embodiment, mast 543a may extend distally and mast 543b may extend proximally. Three masts are useful for a valve module having three leaflets; fewer or more masts may be used with valve modules having fewer or more leaflets.

In their delivery configurations, the first and second self-assembly members 530a, 540a may be substantially straight, as illustrated in FIG. 5B. Alternatively, the mast portions of the first and second self-assembly members may be folded back onto the ring and base portions of the first and second self-assembly members (not shown). In either embodiment, at least the first self assembly member may be attached to the base of the leaflets substructure. The first and second self-assembly members 530a, 540a may be located external of the roll that is the folded leaflets substructure 500a as depicted in FIG. 5B, or the leaflets substructure may be folded (rolled) around the first and second self-assembly members (as illustrated for another self-assembly member embodiment in FIG. 2B). When the leaflets substructure is unfurled, the ring portion 531 of the first self-assembly member 530 may revert to its preset configuration, thereby assembling the leaflets substructure 500 to assume a 3-dimensional working configuration of the valve component 510. The mast portion 533 of the first self-assembly member 530 and the masts 543a, 543b of the second self-assembly member 540 support the commissures of the assembled valve component 510, as shown highly schematically in FIG. 5C, to illustrate both the assembled valve component 510 and the parts of the first and second self-assembly members 531, 533, 543a, 543b beneath. For valve modules having fewer or more leaflets, the first and second self assembly members 530, 540 may be provided with fewer or more mast portions, as appropriate. A similar embodiment of a self-assembly member may be used with valve sections to assemble a valve assembly.

Figure 6A:
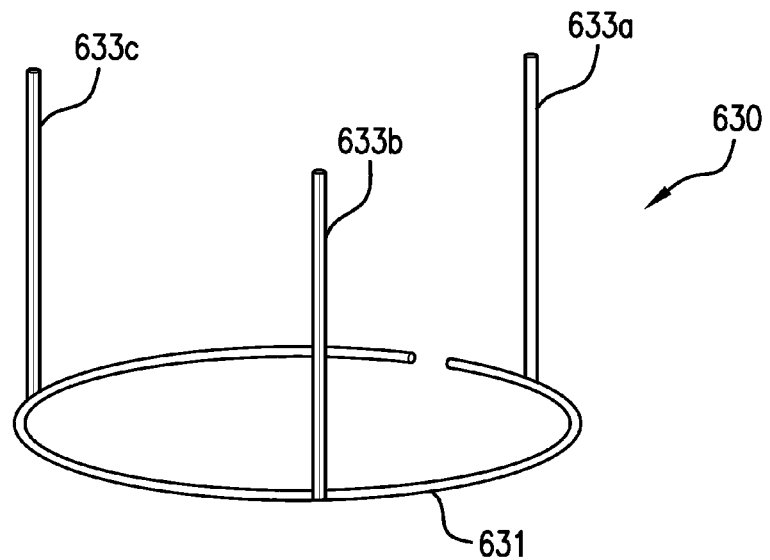
FIGS. 6A and 6B illustrate one embodiment of a self-assembly member for a valve module, that includes a first self-assembly member and commissural masts.
Figure 6B:
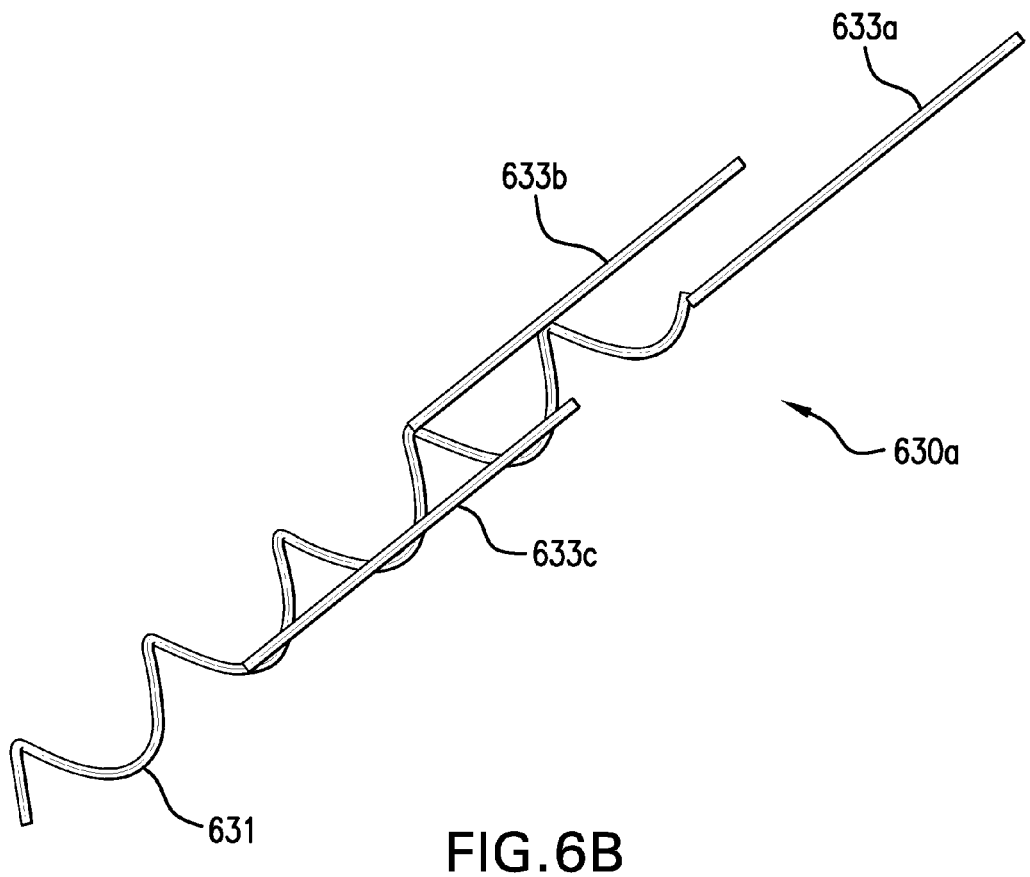

An embodiment of a self-assembly member having a plurality of masts is illustrated in FIGS. 6A and 6B. As shown in its preset configuration in FIG. 6A, the self-assembly member 630 may comprise a ring 631 and a plurality of masts, in this embodiment three masts 633a, 633b, 633c designed for a valve module having three leaflets. The plurality of masts 633a, 633b, 633c are oriented parallel to one another and axially, and, in the preset configuration, perpendicular to the ring 631, extending in the distal direction relative to the ring 631 to provide support to the valve commissures. FIG. 6B shows the self-assembly member 630 in a delivery configuration. Specifically, the ring 631 portion may be constrained in a shaft or a lumen of the delivery device in a geometric form, such as a helix, as illustrated in FIG. 6B, to achieve a small diameter deliver configuration. Upon release from the geometric constraint, the self-assembly member 630 may revert to its preset configuration, as shown in FIG. 6A.

This embodiment of the self-assembly member 630 may be delivered attached to the valve module as the self-assembly member for assembling the valve module, or it may be used as a second self-assembly member in conjunction with a valve module and first self-assembly member that is a simple ring, similar to that illustrated in FIG. 2A-C. Where the curled mast ring self-assembly member of FIGS. 6A and 6B is a second self-assembly member, it may be deployed after the support structure has been deployed and the valve module has been assembled into its working configuration via a first self-assembly member, to provide commissural support to the valve module.

Figure 7:
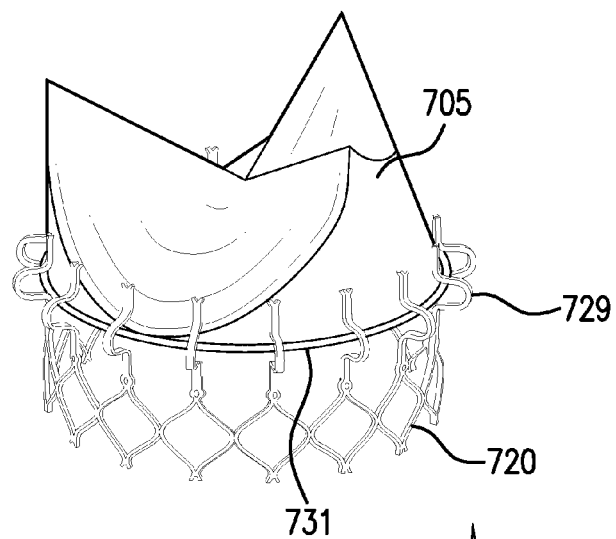
FIG. 7 illustrates an embodiment of a modular valve device that includes a self-assembly member having features for attaching the assembled valve module to a support structure.

An embodiment of a modular valve device comprising a self-assembly member that may also serve to lock the valve module and support structure together is illustrated in FIG. 7. In this embodiment, the self-assembly member includes a ring structure 731 capable of reverting to a preset configuration that assembles the valve module 705 and has a diameter large enough to engage a ring groove 729 attached to the support structure 720. This combination of self-assembly member ring structure 731 attached to the valve module 705 and ring groove 729 of the support structure 720 provides a geometrical lock to attach the valve module 705 to the support structure 720.

Figures 8A, 8B:
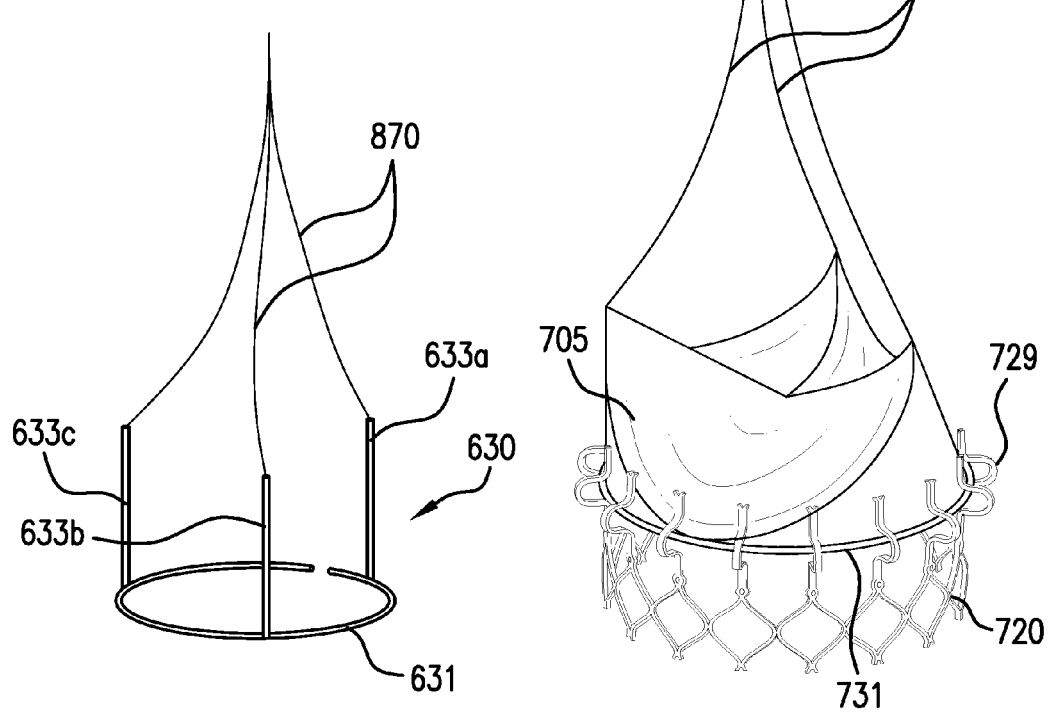
FIGS. 8A-8B illustrate how a valve module may be guided by strings or pull wires during assembly.

FIGS. 8A and 8B illustrate how guiding strings 870 may be used to guide the self-assembly member or valve module during assembly of the valve device. In particular, FIG. 8A depicts one embodiment of guiding strings 870 attached to the masts 633a, 633b, 633c of the self-assembly member 630 embodiment shown in FIG. 6A. The guiding strings 670 may be used to direct or guide the release of the ring 631 and masts 633a, 633b, 633c of the self-assembly member 630. Further, where the self-assembly member 630 is a second self-assembly member, the guiding strings 870 may be used to direct the ring 631 and masts 633a, 633b, 633c into the valve module to support the commissures. FIG. 8B depicts one embodiment of guiding strings 870 attached to commissures of the valve module, for example the valve module 705 of FIG. 7. In this embodiment, the guiding strings 870 may be used to direct the ring release during assembly of the valve module. Guiding strings may also be used in conjunction with other embodiments of the valve device—e.g., valve modules attached to other configurations of self-assembly member(s)—for example, as illustrated in FIG. 5A-5B. In an alternative embodiment (not shown), push-rods may be used in the manner described for guiding strings, or in conjunction with guiding strings. For example, in one embodiment, the guiding strings may be threaded through one or more push-rods having a tubular structure, and the guiding strings may be pulled relative to the one or more push-rods. Alternatively, the guiding strings may be manipulated using mechanisms within the delivery system.

The guiding strings may have a proximal end that extends out the proximal end of the delivery device so that the operator may direct the self-assembly member or other structure attached at the distal end of the guiding strings. Alternatively, guiding strings may be integral to the delivery device. Other arrangements between the guiding strings 870 and self-assembly member or valve module are within the scope of the invention and should be readily discernable to the skilled artisan from the description herein. A tube, referred to as a push-rod, may be used to provide further control of the orientation of the valve module (not shown) via the guiding strings 870, in a manner similar to that described for tubes used with pulling wires, as described in ¶¶74-76 and FIGS. 4B-4C of co-pending U.S. patent application Ser. No. 12/686,335 (modular), filed on date even herewith, which is incorporated herein by reference. Briefly, a tube may be slid over the proximal end of the guiding strings from the proximal end of the delivery device, advanced toward the valve device and used to further manipulate the guide strings 870 and valve module 705. One or more tubes may similarly be used to control guiding strings 870 attached to masts 633a, 633b, 633c to further direct the ring 631 and masts 633a, 633b, 633c of the self-assembly member 630, or to guiding strings 870 attached to other positions on a self-assembly member. The guiding strings 870 may be made of materials similar to the pulling wires, for example, metal, plastic or string, or they may be made of a biodegradable material and left in place to degrade after use. Optionally, guiding strings may be disengaged from the masts of the self-assembly member by electrical current.

Figure 9:
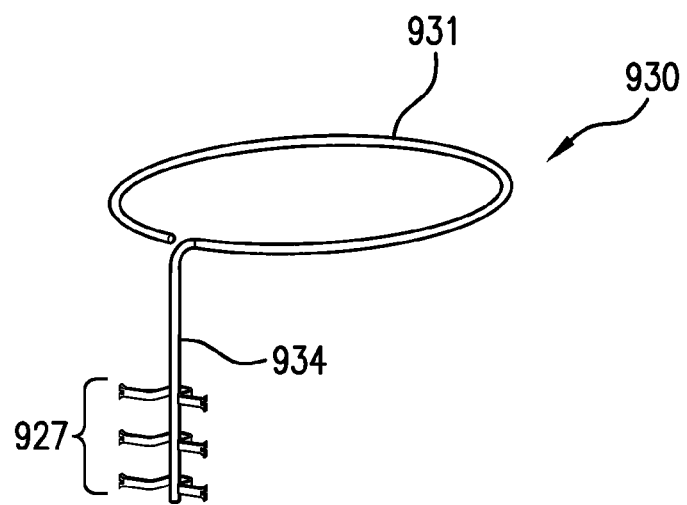
FIG. 9 illustrates one embodiment of a self-assembly member having a ring tab to connect the valve module and the support structure.

The self-assembly member 930 illustrated in FIG. 9 includes a ring structure 931 and a ring tab 934. In its preset configuration, the ring tab 934 is oriented axially and perpendicular to the ring structure 931, extending proximally from the ring structure 931 towards the support structure (not shown for clarity). The ring tab 934 may be inserted into a tab slot 927 on the support structure (in the embodiment depicted here, an axially aligned series of brackets placed in along the inner surface of the support structure) either prior to loading the device modules into the delivery device, or after deployment from the delivery device, and either prior to or after reverting the self-assembly member 930 to its preset configuration and assembling the valve module. The ring structure 931 may be attached to the unassembled valve module prior to folding and loading into the delivery device. This embodiment of the self-assembly member 930 not only permits the valve module and support structure to be folded and compressed separately and delivered unassembled (to minimize the delivery diameter) and effects assembly of the valve module via the ring structure 931, but also facilitates assembly of the valve device from the valve module and support structure via the ring tab 934 and tab slot 927 interaction. In the aspect of this embodiment where the ring tab 934 is inserted into the tab slot 927 prior to delivery, the valve module and support structure may be fixedly connected to one another during delivery; they are connected but do not have the same spatial relationship as in the working configuration, and therefore remain modular (unassembled) and may be folded to a delivery configuration having a smaller delivery diameter.

Figure 10:
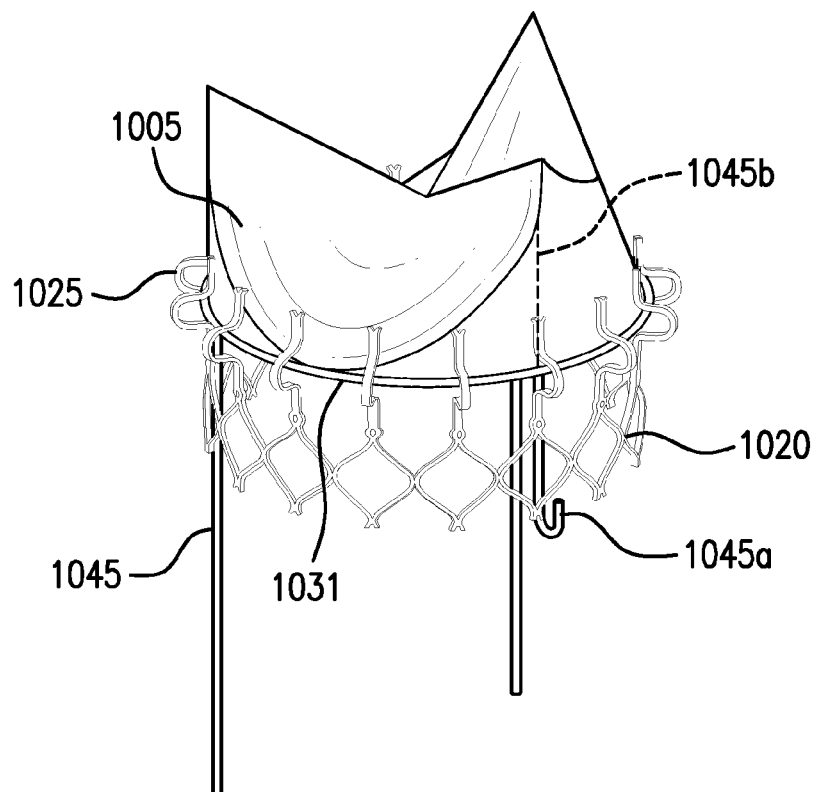
FIG. 10 illustrates one embodiment of a self-assembly member that includes three shape-memory masts that provide support to the valve commissures.

In another embodiment, illustrated in FIG. 10, a first self-assembly member includes a ring structure 1031 and a second self-assembly member includes posts 1045a-c, preferably attached to a ring structure (not shown) and in a preset configuration oriented perpendicular to the ring structure 1031 of the first self-assembly member extending in the proximal direction from the ring structure 1031. In a delivery configuration, the ring structure 1031 of the first assembly member and posts 1045 (and ring) of the second self-assembly member may be straightened to accommodate bundling with the device modules and/or packaging in the delivery device. The ring structure 1031 of the first assembly member preferably is attached to the valve module and may be triggered to assume its preset configuration separately from the second assembly member posts 1045, to assemble the valve module. When the valve module 1005 and support structure 1020 are combined to form the assembled valve device, the second self assembly member may be triggered to revert to its preset configuration 1045a, 1045b. Thus, the proximal end of the post 1045a may revert to a preset bent or curled configuration to engage the support structure 1020 and the distal end of the post 1045b may revert to a preset configuration in which it bends back in the distal direction, similar to the opening of a folding walking stick. The distal end of the post 1045b ends up perpendicular to the ring structure 1031 of the first self-assemble member, but extending in the distal direction, to provide support to the valve commissures.

In any of the embodiments of self-assembly members, the self-assembly member may be attached to a leaflets substructure, leaflets ring, or a plurality of valve sections, for use in assembling the valve module, and/or combining the valve module and support structure into an assembled valve device.

The method of delivering and assembling a modular prosthetic valve device using a self-assembly member, may be illustrated with reference to an embodiment of the valve device comprising the valve assembly 115 of FIG. 1. One embodiment of such a method, for example, may proceed as follows: A delivery device, such as a catheter, carrying a support structure and a plurality of valve sections and a self-assembly member may be introduced into a body lumen and advanced to a desired location in the body, e.g., at or near the final location where the valve device is to be implanted. The support structure may be deployed first so as to be capable of receiving the valve sections. Once the support structure is in place, the valve sections may be deployed from the delivery device. After being deployed from the delivery device, the self-assembly member may be triggered to revert to its preset configuration, thereby positioning the valve sections in the shape of an assembled valve. The valve sections may be assembled into the valve assembly within the support structure or they may be assembled outside the support structure and then positioned in the support structure. Once the valve assembly is formed, the valve sections may be attached to one another via locking mechanisms. If the valve assembly is formed outside the support structure, it may be positioned in and combined with the support structure, for example using pull wires, guiding strings as shown FIGS. 8A and 8B, or push-rods. The valve assembly and support structure then may be locked together with locking mechanisms, as discussed below. The use of self-assembly members in a similar manner to assemble and position a modular valve device having fewer or more than four device modules is well within the scope of the invention. Where appropriate, more than two self-assembly members may be used to assemble the device modules.

A method of assembling a modular valve device comprising a leaflets substructure using the simple self-assembly member as illustrated in FIGS. 2A-2C may proceed in a similar manner. Methods of assembling a modular valve device using one or more self-assembly members as described in FIGS. 3A-B, 5-8 or other embodiments of self-assembly members may also proceed similarly and is well within the skill in the art in view of the descriptions herein.

Pull wires (as described in detail in ¶¶54, 65, 67-68, 71-76 and FIGS. 4b-c of co-pending U.S. patent application Ser. No. 12/686,335 (modular), filed on date even herewith, which is incorporated herein by reference) are not required for assembly of valve sections into a valve assembly in accordance with the invention, however where pull wires are used, they may be threaded through the valve assembly and support structure in a manner that loosely tethers them for delivery. Pull wires also may be used to assist in the assembly of the valve assembly and support structure. The pull wires may be tethered to the device modules by any appropriate means known in the art, for example, by threading the wires through loops in each one of the device modules, which connection is reversible by pulling on just one end of the wire for removal of the pull wires after the device is implanted and secured to the body lumen. The device modules may comprise loops or small holes through which the pull wires are threaded.

Suitable locking mechanisms for attaching the first and second ends of the leaflets substructure, for attaching the valve sections together, and for attaching the valve module to the support structure are described in detail in ¶¶48-51, 84-113 and FIGS. 7-15 of co-pending application Ser. No. 12/686,335 (modular), filed on date even herewith, which is incorporated herein by reference. In particular, such locking mechanisms may include male-female coupling type components; slotted hook mechanisms; interlocking curvilinear groove (zip-lock) mechanism; interference-fit; press-fix connectors; snap-fit mechanism; hook-and-eye components; fish-hook; hook-and-groove components; a locking tab; stud-and-harbor lock; and interconnecting or interlocking geometries (e.g., dovetail or pins, pegs, rivets or stud-and-tube connectors). The interlocking curvilinear groove (zip-lock) mechanism may be particularly useful for attaching together the ends 251, 252 of the leaflets substructure 200 or the sides of valve sections. The locking mechanisms preferably are of the kind that is easily engaged from a remote location, yet also provides a secure fitting that will not disengage during use.

In any of the embodiments, it is possible and may be desirable to connect the valve module to the support structure adjustably so as to allow the final accurate positioning of the valve module. Thus, for example, the valve assembly may be connected to the support structure in an adjustable manner that will allow final adjustments of position of the valve assembly relative to the support structure after implantation of the valve device. Mechanisms for adjusting the position of the valve module relative to the support structure are described in detail in ¶¶21-24, 28-39 and FIGS. 1a-7 of co-pending U.S. application Ser. No. 12/686,340, entitled "Method and Apparatus for Fine Adjustment of a Percutaneous Valve Structure", filed on date even herewith, which application is incorporated herein by reference. The support structure also may be adjustably connected to the vessel wall.

It is important that a prosthetic valve device is placed in a vessel (or lumen) with precision to ensure proper valve function and safety to the patient. Accordingly, the device and system of the invention, as well as the method of assembling the device, may be used in conjunction with the placement system and method of placing a modular device, which are described in ¶¶22-42 and FIGS. 1a-2 of co-pending U.S. application Ser. No. 12/686,337 (placement), entitled "A System and Method for Placing a Percutaneous Valve Device," filed on date even herewith, which applications are incorporated herein by reference. As described in co-pending U.S. application Ser. No. 12/686,337 (placement), the method of placing a prosthetic valve device in a body lumen with improved accuracy comprises, for example, affixing an anchor in a body lumen at a location of valve implantation; and using said anchor to guide said prosthetic valve device to said location of valve implantation. Anchors may include a button or rivet-type device, a hook, a percutaneously-inserted leading suture, interconnecting geometries, or any other type of docking apparatus device. In some embodiments, the anchor may be connected to a placement wire.

It will be appreciated by persons having ordinary skill in the art that many variations, additions, modifications, and other applications may be made to what has been particularly shown and described herein by way of embodiments, without departing from the spirit or scope of the invention. Therefore it is intended that scope of the invention, as defined by the claims below, includes all foreseeable variations, additions, modifications or applications.

What is claimed is:

1. A modular percutaneous prosthetic valve device, comprising a plurality of components, said components including a valve module and a self-assembly member, each in a delivery configuration for mounting in a delivery device, said valve module having a leaflet substructure and a folded, unassembled delivery configuration designed to unfold into a working configuration after deployment from said delivery device due to a configuration change of said self-assembly member, said self-assembly member selected from a group consisting of a wire, a band or a strip and having a delivery configuration extending in a generally linear direction along a longitudinal axis of said delivery device, wherein said self-assembly member moves from said delivery configuration to said working configuration after deployment from said delivery device, wherein the self-assembly member is attached to the leaflet substructure in the working configuration.

2. The device of claim 1, wherein said folded, unassembled valve module is formed by substantially flattening said unassembled valve module and folding.

3. The device according to claim 2, wherein said valve module comprises a plurality of valve sections, each of said valve sections having a first end, a section height axis and a section circumferential axis, said substantially flattened, unassembled configuration comprising said plurality of valve sections arranged end to end in a series, said circumferential axis of said substantially flat, unassembled configuration comprising the sum of said section circumferential axes and extending from the first end of a first valve section of said series to the second end of the last valve section of said series, and said height axis of said substantially flat, unassembled configuration is equivalent to each of said section height axes; wherein said plurality of valve sections is designed for assembly via said self-assembly member into said working configuration valve assembly.

4. The device according to claim 2, wherein said valve module comprises a leaflets substructure having a one-layer substantially flattened, unassembled configuration; wherein said leaflets substructure is designed for assembly via said self-assembly member into a working configuration valve component.

5. The device according to claim 2, wherein said valve module comprises a leaflets-ring having a two-layer substantially flattened, unassembled configuration and said self-assembly member includes two flexure portions each capable of forming a bend when said leaflets-ring is substantially flattened, unassembled configuration; wherein said leaflets-ring is designed for assembly via said self-assembly member into a working configuration valve component.

6. The device of claim 2, wherein said substantially flattened unassembled configuration comprises an apex-base aspect, a circumferential axis, and a height axis, and said folded, unassembled delivery configuration is rolled along a single axis.

7. The device of claim 3, wherein said substantially flat, unassembled configuration is rolled in a manner selected from the group consisting of: from apex to base; in the direction of said height axis; in the direction of said circumferential axis; and overlapping.

8. The device of any one of claims 1-7, wherein said self-assembly member is attached to said valve module.

9. The device of any one of claims 1-5, wherein said self-assembly member comprises a shape-memory alloy.

10. The device according to claim 2, 3, 4 or 5, wherein said valve device further comprises an expandable support structure, said support structure having a compressed, unexpanded delivery configuration for mounting in said delivery device and capable of being expanded for assembly and implantation after deployment from said delivery device; said expanded support structure designed for combination with said valve module in said working configuration to form said valve device.

11. The device of claim 10, wherein said self-assembly member is a first self-assembly member, said device further comprising a second self-assembly member.

12. The device of claim 11, wherein said first and second self-assembly members comprise a shape-memory alloy.

13. The device of claim 5, wherein said first self-assembly member extends in a generally linear direction along a longitudinal axis of the delivery device in the delivery configuration and a ring-shaped configuration in a pre-set configuration, and wherein said second self-assembly member extends in a generally linear direction along a longitudinal axis of the delivery device in the delivery configuration and has a pre-set configuration selected from the group consisting of a mast, a post, and a mast and post, wherein in said delivery configuration said second self-assembly member lies parallel to said longitudinal axis.

14. The device of claim 13, wherein said first and second self-assembly members each comprise a shape-memory alloy.

15. The device of claim 13, wherein said second self-assembly member comprises a post having a proximal post end and a distal post end, wherein when in said delivery configuration said second self-assembly member is folded so that said distal post end lies approximately parallel to said proximal post end and said distal and proximal post ends are substantially straight, and when in said pre-set configuration said second self-assembly member is unfolded so that said distal post end extends distally from said proximal post end to provide support to a valve commissure and said proximal post end has a curve to engage said support structure.

16. A modular percutaneous valve device, comprising:
a folded valve module for mounting in a delivery device, and capable of unfolding for assembly after delivery to an unfolded, substantially flat unassembled configuration, having a base, apex, circumferential axis and a height axis extending from the base to the apex, and a folded configuration rolled in the direction of said height axis from the base to the apex or the apex to the base.

17. The device of claim 16, wherein said folded valve module comprises a leaflets substructure capable of being assembled into a valve component; said valve device further comprising:
an expandable support structure, said support structure being compressed for mounting in said delivery device; wherein said valve device is capable of being assembled from said assembled valve component and said support structure in an expanded state after deployment from said delivery device.

18. The modular percutaneous valve device of claim 16, wherein said unfolded, substantially flat unassembled valve module comprises a plurality of valve sections in series, said plurality of valve sections capable of being assembled into a valve assembly, wherein each of said valve sections has a section height axis and a section circumferential axis; wherein said circumferential axis comprises the sum of said section circumferential axes, and said height axis is equivalent to each of said section height axes.

19. A system for assembling a percutaneous prosthetic valve device in a body in need thereof, said system comprising a delivery device and the valve device of claim 10.

20. The system according to claim 19, further comprising a guiding string.

21. The system according to claim 19, further comprising a push-rod.

22. A method of folding a valve module of a modular valve device for delivery in a percutaneous delivery device comprising:
providing a valve device that when substantially flattened has a base, apex, height axis extending from the base to the apex and a circumferential axis;
folding said valve module in a manner selected from the group consisting of: rolling said unassembled, substantially flattened valve in the direction of said height axis, and squashing said valve module prior to loading into said delivery device.

23. A self-assembly member for assembling a valve module of a modular prosthetic percutaneous valve device after deployment from a delivery device, wherein said self-assembly member is selected from a group consisting of a wire, a band or a strip and has a delivery configuration and a preset configuration, and wherein when in said preset configuration said self-assembly member comprises a ring portion, and in said delivery configuration said ring portion opens up to extend in a generally linear direction along the longitudinal axis of said delivery device.

24. The self-assembly member of claim 23, wherein said self-assembly member further comprises a mast, said mast oriented parallel to the longitudinal axis of said delivery device in said delivery configuration and oriented perpendicularly to said ring portion of said self-assembly member in said preset configuration to support a valve commissure.

25. The self-assembly member of claim 24, wherein said mast in said delivery configuration is further folded back and unfolds after deployment to said pre-set configuration.

26. The self-assembly member of claim 23, wherein said self-assembly member comprises a first self-assembly member and a second self-assembly member, said first self-assembly member comprising in said preset configuration said ring portion and said second self-assembly member comprising a mast oriented parallel to the longitudinal axis of said delivery device in said delivery configuration and having at least a portion oriented perpendicularly to said ring portion in said preset configuration.

27. The self-assembly member of claim 23, wherein said self-assembly member further comprises a post, said post oriented parallel to a longitudinal axis of said delivery device in said delivery configuration and oriented perpendicularly to said ring portion of said self-assembly member in said pre-set configuration to engage a support structure.

28. A method of assembling a modular valve device comprising:
providing a percutaneous delivery device containing a valve module and a self-assembly member, said valve module having a leaflets substructure, said self-assembly member is selected from a group consisting of a wire, a band or a strip, said self-assembly member extending in a generally linear direction along a longitudinal axis of said delivery device in the delivery configuration, and said valve module in a folded, unassembled delivery configuration;

deploying said folded, unassembled delivery configuration of said valve module from said delivery device;

unfolding said folded, unassembled delivery configuration of said valve module to form an unfolded valve module;

reverting said self-assembly member to a preset configuration; and assembling said unfolded valve module into a working configuration using said self-assembly member, wherein the self-assembly member is attached to the leaflet substructure in the working configuration.

29. The method of claim 28, wherein said folded, unassembled delivery configuration is formed by substantially flattening an unassembled configuration to comprise a base-to-apex aspect, a circumferential axis and a height axis, and folding.

30. The method of any one of claim 28 or 29, wherein said folded, unassembled delivery configuration is a substantially flattened, unassembled valve module rolled along a single axis.

31. The method of claim 29, wherein said delivery device further contains an expandable support structure compressed to an unexpanded delivery configuration, said method further comprising:

deploying said unexpanded delivery configuration of said support structure from said delivery device;

expanding said support structure to form an expanded support structure; and combining said expanded support structure with said valve component to form an assembled valve device.

32. The method of claim 29, said delivery device further comprising an expandable support structure compressed to an unexpanded delivery configuration, said method further comprising:

deploying said unexpanded support structure from said delivery device;

expanding said support structure to form an expanded support structure; and combining said expanded support structure with said valve assembly to form an assembled valve device.

33. A method of assembling a modular prosthetic valve device in a body in need thereof, comprising: providing a delivery device containing a plurality of device modules and a self-assembly member, said self-assembly member in a delivery configuration, said plurality of device modules comprising an expandable support structure compressed to an unexpanded configuration and a leaflets substructure in a folded configuration, wherein when laid out in an unassembled, unfolded substantially flat configuration said leaflets substructure has a height axis and a circumferential axis and said self-assembly member is attached to said leaflets substructure circumferential axis, and wherein said folded configuration of said leaflets substructure comprises rolling in the direction of said height axis prior to loading into said delivery device; deploying said unexpanded support structure and said folded leaflets substructure from said delivery device; expanding said support structure; unfurling said folded leaflets substructure and triggering said self-assembly member to revert to a preset configuration; assembling said leaflets substructure to form a valve component using said self-assembly member; and combining said valve component and said support structure to form an assembled valve device.

34. A modular percutaneous prosthetic valve device, comprising:

a folded valve module, said folded valve module having a folded, delivery configuration, wherein said folded valve module is capable of unfolding for assembly after delivery from a delivery device to an unfolded, substantially flat unassembled configuration; and a self-assembly member for assembling said folded valve module after delivery from said delivery device, said self-assembly member selected from a group consisting of a wire, a band, or a strip and having a delivery configuration and a preset configuration, wherein when in said preset configuration said self-assembly member comprises a ring portion, and in said delivery configuration said ring portion opens up to extend in a generally linear direction along a longitudinal axis of said delivery device.

35. A modular percutaneous prosthetic valve device, comprising a valve module and a self-assembly member, each in a delivery configuration for mounting in a delivery device, said valve module having a folded delivery configuration capable of unfolding for self-assembly and being assembled into a working configuration via said self-assembly member after deployment from said delivery device, said self-assembly member comprising a ring portion in said working configuration, said self-assembly member having a straight delivery configuration parallel to a longitudinal axis of said delivery device, and the valve module is in a squashed configuration when in the folded delivery configuration.

* * * * *